(12) United States Patent
Chevolleau et al.

(10) Patent No.: US 10,914,720 B2
(45) Date of Patent: Feb. 9, 2021

(54) METHOD TO EVALUATE THE STABILITY OF A PROTEIN-BASED FORMULATION

(71) Applicant: Becton Dickinson France, Le Pont de Claix (FR)

(72) Inventors: Tzvetelina Chevolleau, Saint Egreve (FR); Jean-Bernard Hamel, Saint Cassien (FR)

(73) Assignee: Becton Dickinson France, Le Pont de Claix (FR)

( * ) Notice: Subject to any disclaimer, the term of this patent is extended or adjusted under 35 U.S.C. 154(b) by 254 days.

(21) Appl. No.: 16/075,799

(22) PCT Filed: Feb. 10, 2017

(86) PCT No.: PCT/EP2017/053021
§ 371 (c)(1),
(2) Date: Aug. 6, 2018

(87) PCT Pub. No.: WO2017/137570
PCT Pub. Date: Aug. 17, 2017

(65) Prior Publication Data
US 2019/0064138 A1 Feb. 28, 2019

(30) Foreign Application Priority Data
Feb. 10, 2016 (EP) ..................... 16305152

(51) Int. Cl.
| G01N 33/30 | (2006.01) |
| G01N 33/15 | (2006.01) |
| G01N 33/68 | (2006.01) |
| G01N 13/02 | (2006.01) |
| A61K 39/00 | (2006.01) |
| A61K 47/26 | (2006.01) |

(52) U.S. Cl.
CPC .............. *G01N 33/30* (2013.01); *A61K 39/00* (2013.01); *A61K 47/26* (2013.01); *G01N 13/02* (2013.01); *G01N 33/68* (2013.01); *G01N 33/15* (2013.01)

(58) Field of Classification Search
CPC ........ A61K 39/00; A61K 47/26; G01N 13/02; G01N 33/15; G01N 33/30; G01N 33/68
USPC ..................... 436/60, 86, 174, 176
See application file for complete search history.

(56) References Cited

U.S. PATENT DOCUMENTS

| 4,959,402 A | 9/1990 | Williams et al. |
| 4,994,552 A | 2/1991 | Williams et al. |
| 5,034,482 A | 7/1991 | Kohara et al. |
| 5,338,312 A | 8/1994 | Montgomery |
| 5,540,494 A | 7/1996 | Purvis, Jr. et al. |
| 5,599,882 A | 2/1997 | Nishi et al. |
| 5,610,253 A | 3/1997 | Hatke et al. |
| 5,623,039 A | 4/1997 | Hatke et al. |
| 5,650,471 A | 7/1997 | Abe et al. |
| 5,853,481 A | 12/1998 | Williamitis et al. |
| 5,854,349 A | 12/1998 | Abe et al. |
| 5,856,414 A | 1/1999 | Hatke et al. |
| 5,866,662 A | 2/1999 | Hatke et al. |
| 6,005,113 A | 12/1999 | Wu et al. |
| 6,063,886 A | 5/2000 | Yamaguchi et al. |
| 6,461,334 B1 | 10/2002 | Buch-Rasmussen et al. |
| 6,486,264 B1 | 11/2002 | Tsunogae et al. |
| 6,511,756 B1 | 1/2003 | Obuchi et al. |
| 6,525,084 B2 | 2/2003 | Rasmussen et al. |
| 6,525,144 B1 | 2/2003 | Tanahashi et al. |
| 6,638,519 B1 | 10/2003 | Lorant |
| 6,653,424 B1 | 11/2003 | Sakamoto et al. |
| 6,908,970 B2 | 6/2005 | Tsunogae et al. |
| 6,951,898 B2 | 10/2005 | Hammond et al. |
| 6,995,226 B2 | 2/2006 | Taguchi et al. |
| 7,026,401 B1 | 4/2006 | Osan et al. |
| 7,037,993 B2 | 5/2006 | Taguchi et al. |
| 8,030,095 B2 | 10/2011 | Harriman |
| 8,354,239 B2 | 1/2013 | Gaylord et al. |
| 8,633,034 B2 | 1/2014 | Trotter et al. |
| 2002/0037401 A1 | 3/2002 | Buch-Rasmussen et al. |
| 2003/0054979 A1* | 3/2003 | Kim ............... A61K 9/0019 514/6.5 |
| 2003/0072807 A1 | 4/2003 | Wong et al. |

(Continued)

FOREIGN PATENT DOCUMENTS

| EP | 0982041 A1 | 3/2000 |
| EP | 1811297 A1 | 7/2007 |

(Continued)

OTHER PUBLICATIONS

Depaz et al. Journal of Pharmaceutical Sciences, vol. 103, Mar. 18, 2014, pp. 1384-1393.*
Arakawa et al., "Factors affecting short-term and long-term stabilities of proteins", Advanced Drug Delivery Reviews, 1993, pp. 1-28, vol. 10.
Baldwin, "Contamination of insulin by silicone oil: a potential hazard of plastic insulin syringes", Diabetic Medicine, 1988, pp. 789-790, vol. 5:8.
Bernstein, "Clouding and Deactivation of Clear (Regular) Human Insulin: Association With Silicone Oil From Disposable Syringes?", Diabetes Care, 1987, pp. 786-787, vol. 10:6.

(Continued)

*Primary Examiner* — Maureen Wallenhorst
(74) *Attorney, Agent, or Firm* — The Webb Law Firm

(57) ABSTRACT

Disclosed herein is a method to evaluate the stability of a protein-based formulation including a protein, a peptide and/or a protein derivative and a buffer relative to a lubricant of a lubricated container in which the formulation is intended to be stored, including: a) Evaluating a decrease over time of interfacial tension between the buffer and the lubricant, b) Evaluating a decrease over time of interfacial tension between the protein-based formulation and the lubricant, c) Identifying at least one component of the protein-based formulation interacting with the lubricant by comparing the decrease evaluated in step b) with the decrease evaluated in step a).

8 Claims, 9 Drawing Sheets

(56) References Cited

U.S. PATENT DOCUMENTS

| | | | |
|---|---|---|---|
| 2003/0186904 A1 | 10/2003 | Ruben et al. | |
| 2005/0053598 A1 | 3/2005 | Burke et al. | |
| 2005/0065192 A1 | 3/2005 | Yednock et al. | |
| 2005/0069935 A1 | 3/2005 | Boehm et al. | |
| 2005/0074451 A1 | 4/2005 | Yednock et al. | |
| 2005/0123947 A1 | 6/2005 | Quake et al. | |
| 2005/0276812 A1 | 12/2005 | Ebens, Jr. et al. | |
| 2006/0051353 A1 | 3/2006 | Colombel et al. | |
| 2006/0200084 A1 | 9/2006 | Ito et al. | |
| 2009/0111768 A1 | 4/2009 | Caldwell et al. | |
| 2010/0255477 A1 | 10/2010 | Bazan et al. | |
| 2011/0106044 A1 | 5/2011 | Trotter et al. | |
| 2017/0173267 A1* | 6/2017 | Ashmead | A61K 35/12 |
| 2017/0182252 A1* | 6/2017 | Hamel | A61M 5/3129 |

FOREIGN PATENT DOCUMENTS

| | | | |
|---|---|---|---|
| JP | 57106622 A | 7/1982 | |
| JP | 63264626 A | 11/1988 | |
| JP | 1158029 A | 6/1989 | |
| JP | 3115338 A | 5/1991 | |
| JP | 3121122 A | 5/1991 | |
| JP | 838600 A | 2/1996 | |
| JP | 8109222 A | 4/1996 | |
| JP | 8183812 A | 7/1996 | |
| JP | 8231652 A | 9/1996 | |
| JP | 10287713 A | 10/1998 | |
| JP | 11218601 A | 8/1999 | |
| JP | 2001504326 A | 4/2001 | |
| JP | 2002241264 A | 8/2002 | |
| JP | 2003504443 A | 2/2003 | |
| JP | 2003513294 A | 4/2003 | |
| JP | 2004321614 A | 11/2004 | |
| JP | 2006182960 A | 7/2006 | |
| JP | 2007536555 A | 12/2007 | |
| JP | 4174968 B2 | 11/2008 | |
| JP | 4557124 B2 | 10/2010 | |
| JP | 4691867 B2 | 6/2011 | |
| WO | 9717610 A1 | 5/1997 | |
| WO | 9944754 A1 | 9/1999 | |
| WO | 9944755 A1 | 9/1999 | |
| WO | 0117542 A1 | 3/2001 | |
| WO | 03007868 A1 | 1/2003 | |
| WO | 2004103398 A1 | 12/2004 | |
| WO | 2007082757 A2 | 7/2007 | |
| WO | 2008072503 A1 | 6/2008 | |
| WO | 2009003010 A2 | 12/2008 | |

OTHER PUBLICATIONS

Chantelau, "Silicone oil contamination of insulin", Diabetic Medicine, 1989, pp. 278, vol. 6:3.
Chantelau et al., "Silicone Oil Released From Disposable Insulin Syringes", Diabetes Care, 1986, pp. 672-673, vol. 9:6.
Chantelau et al., "Pollution of Insulin with Silicone Oil, a Hazard of Disposable Plastic Syringes", The Lancet, 1985, pp. 1459.
Chi et al., "Roles of conformational stability and colloidal stability in the aggregation of recombinant human gramulocyte colony-stimulating factor", Protein Science, 2003, pp. 903-913, vol. 12.
Chi et al., "Physical Stability of Proteins in Aqueous Solution: Mechanism and Driving Forces in Nonnative Protein Aggregation", Pharmaceutical Research, 2003, pp. 1325-1336, vol. 20:9.
Chi et al., "Heterogeneous Nucleation-Controlled Particulate Formation of Recombinant Human Platelet-Activating Factor Acetylhydrolase in Pharmaceutical Formulation", Journal of Pharmaceutical Sciences, 2005, pp. 256-274, vol. 94:2.
Chou et al., "Effects of Tween 20® and Tween 80® on the Stability of Albutropin During Agitation", Journal of Pharmaceutical Sciences, 2005, pp. 1368-1381, vol. 94:6.
Doornbos et al., "Lissajous-Like Patterns in Scatter Plots of Calibration Beads", Cytometry, 1994, pp. 236-242, vol. 16.
Furness (Editor), "Prefilled syringes: innovations that meet the growing demand", ONdrugDelivery Ltd, 2005, pp. 1-28.
Gabrielson et al., "Silicone oil contamination of therapeutic protein formulations: Surfactant and protein effects", The 234th ACS National Meeting, 2007, pp. BIOT-227.
Hermeling et al., "Structure-Immunogenicity Relationships of Therapeutic Proteins", Pharmaceutical Research, 2004, pp. 897-903, vol. 21:6.
Jett et al., "Quantitation of Cell Surface Antigen Density by Flow Cytometry", 4th International Symposium of Flow Cytometry, 1979, pp. 1-15.
Jones et al., "Silicone Oil Induced Aggregation of Proteins", Journal of Pharmaceutical Sciences, 2005, pp. 918-927, vol. 94:4.
Kim et al., "Thermodynamic Modulation of Light Chain Amyloid Fibril Formation", The Journal of Biological Chemistry, 2000, pp. 1570-1574, vol. 275:3.
Krishnan et al., "Aggregation of Granulocyte Colony Stimulating Factor under Physiological Conditions: Characterization and Thermodynamic Inhibition", Biochemistry, 2002, pp. 6422-6431, vol. 41.
Li et al., "Mechanistic understanding of protein-silicone oil interactions", Pharmaceutical Research, 2012, pp. 1689-1697, vol. 29:6.
Liebmann-Vinson, "Physics of Friction Applied to Medical Devices", Microstructure and Microtribology of Polymer Surfaces, 1999, pp. 474-494.
Schellekens, "When biotech proteins go off-patent", TRENDS in Biotechnology, 2004, pp. 406-410, vol. 22:8.
Wang et al., "Antibody Structure, Instability, and Formulation", Journal of Pharmaceutical Sciences, 2007, pp. 1-26, vol. 96:1.
Ye et al., "Influence of Polysaccharides on the Rate of Coalescence in Oil-in-Water Emulsions Formed with Highly Hydrolyzed Whey Proteins", Journal of Agricultural and Food Chemistry, 2004, pp. 5491-5498, vol. 52.
Zhang et al., "Mechanism for Benzyl Alcohol-Induced Aggregation of Recombinant Human Interleukin-1 Receptor Antagonist in Aqueous Solution", Journal of Pharmaceutical Sciences, 2004, pp. 3076-3089, vol. 93:12.

* cited by examiner

METHOD TO EVALUATE THE STABILITY OF A PROTEIN-BASED FORMULATION

CROSS-REFERENCE TO RELATED APPLICATIONS

This application is the United States national phase of International Application No. PCT/EP2017/053021 filed Feb. 10, 2017, and claims priority to European Patent Application No. 16305152.7 filed Feb. 10, 2016, the disclosures of which are hereby incorporated in their entirety by reference.

FIELD OF THE INVENTION

The invention relates to a method to evaluate the stability of a protein-based formulation relative to a lubricant of a lubricated container in which said formulation is intended to be stored. The invention further relates to a method to adapt a protein-based formulation to a lubricant of a lubricated container and a method to select a lubricant adapted to lubricate a container intended to store a protein-based formulation in order to improve the stability of said formulation relative to the lubricant.

TECHNICAL BACKGROUND

Prefilled injection devices are common containers to deliver drugs or vaccines to patients and include syringes, cartridges and autoinjectors. They usually comprise a sealing stopper in gliding engagement into a container, the container being filled with a pharmaceutical composition in order to provide the practitioners with a ready-to-use injection device.

When compared to empty injection devices that are filled with a vial-stored pharmaceutical composition just prior to the injection, the use of prefilled injection devices leads to several advantages. In particular, by limiting the preparation prior to the injection, the prefilled injection devices provide a reduction of medical dosing errors, a minimized risk of microbial contamination and an enhanced convenience of use for the practitioners. Furthermore, such prefilled containers encourage and simplify self-administration by the patients which allows reducing the cost of therapy and increasing the patient adherence. Finally, prefilled injection devices reduce loss of valuable pharmaceutical composition that usually occurs when a pharmaceutical composition is transferred from a vial to a non-prefilled injection device. This results in a greater number of possible injections for a given manufacturing batch of pharmaceutical product thus reducing buying and supply chain costs.

However, along with these improvements, the commercialization of pharmaceutical composition in prefilled injection devices imparts its own set of challenges, particularly in the case of sensitive biologics. Indeed, biologics such as cytokines, monoclonal antibodies, nucleic acid-based products and vaccines are highly complex molecules and are subject to a variety of degradation pathways that may impact therapy efficacy and patient safety.

For example, in the case of a prefilled syringe, components such as tungsten, silicone-based lubricant and adhesives have all been identified as potential sources of incompatibility for biologics. Lubricants in general and more particularly silicone oils have received increased attention from formulation scientists in order to understand their compatibility with proteins and vaccines. Medical grade silicone oils such as poly-(dimethylsiloxane) (PDMS) are commonly used in injection devices for their lubricant properties: they ensure an efficient gliding of the stopper throughout the injection device barrel during the injection of the pharmaceutical composition to a patient. Silicone oils, however, have been reported to be involved in the degradation of therapeutic proteins, such as the formation of particles in pharmaceutical formulations including vaccines. These particles often comprise aggregated proteins with adjuvants and/or silicone oil.

In addition to significant losses in protein activity, undesired clinical effects and safety concerns may result from parenteral administration of such aggregated proteins. Furthermore, aggregation levels even at very low percentage, such as 1% may render a pharmaceutical composition unacceptable regarding the current best practices and regulations. However, the evaluation of the stability of a protein-based formulation when stored in a lubricated container may be difficult and time-consuming. Furthermore, the adaptation of a protein-based formulation to such containers is often empirical and performed at a late stage of the product development. Some protein-based pharmaceutical compositions may thus be brought to the latter stages of developments before identifying major stability problems when stored in an injection device. This may result in costly reformulation steps and unavailability of precious pharmaceutical compositions for patients.

Finally, when several lubricants are available, no quick method is available to select the most appropriate lubricant for a given protein-based composition. Time-consuming stability studies must thus be performed by medical companies on various injections devices and lubricant compositions without any possibility to short-list the most promising solutions.

As a consequence, there is a strong need for a fast and efficient method to evaluate the stability of a protein-based formulation relative to a lubricant of a lubricated container in which said formulation is intended to be stored. In addition, there is a need for a reliable method to guide the formulation of protein-based formulations intended to be stored in lubricated containers. Finally, a method to select the most appropriate lubricant for a container intended to store a protein-based formulation is also desirable.

BRIEF DESCRIPTION OF THE INVENTION

A first aspect of the present invention is therefore a method to evaluate the stability of a protein-based formulation comprising a protein, a peptide and/or a protein derivative and a buffer relative to a lubricant of a lubricated container in which said formulation is intended to be stored, comprising:
  a) Evaluating a decrease over time of interfacial tension between the buffer and the lubricant,
  b) Evaluating a decrease over time of interfacial tension between the protein-based formulation and the lubricant,
  c) Identifying at least one component of the protein-based formulation interacting with the lubricant by comparing the decrease evaluated in step b) with the decrease evaluated in step a)

This method provides a very good insight of the stability of a protein-based formulation relative to a lubricant of a lubricated container with simple and inexpensive interfacial tension measurements. In particular, this method allows determining whether an interaction happens between the protein and the lubricant, or between the buffer and the lubricant. It thus allows detecting stability problems at a very early stage of the formulation development and avoiding expensive reformulation steps during the latter stages of the formulation development. This method is thus valuable to mitigate the stability risk during the development of a protein-based formulation and save time and money for pharmaceutical companies.

In an embodiment, this method further comprises evaluating the decrease of interfacial tension between each component of the buffer and the lubricant in step a). Indeed, the instability of a protein-based formulation and a lubricant may be linked with any component of the formulation and not only with the protein. This method is thus useful to identify the interacting component(s) among all the components of the buffer.

A second aspect of the present invention is a method to improve the stability of the protein-based formulation relative to the lubricant of said container. In a first approach, this method comprises:

a) Evaluating the stability of a protein-based formulation according to the first aspect of the present invention,
b) Selecting an adjuvant bringing a higher decrease over time of interfacial tension with the lubricant than the protein-based formulation,
c) Adapting the protein-based formulation by adding said selected adjuvant to the protein-based formulation.

This adjuvant may be already present in the buffer and its concentration may thus be increased so as to compete with the interaction detected in the first aspect of the present invention, for example the interaction between the protein and the lubricant. The undesired interaction is therefore replaced by a non-sensitive interaction which does not impede the stability or the potency of the protein-based formulation. The added adjuvant may also be an adjuvant not present in the protein-based formulation before the adaptation of the formulation by the present method. For example, the adjuvant may be a surfactant, such as Polysorbate 80.

In a second approach, this method comprises:

a) Evaluating the stability of a protein-based formulation according to the first aspect of the present invention,
b) Selecting an adjuvant capable of complexing the protein of the protein-based formulation,
c) Adapting the protein-based formulation by adding said selected adjuvant so as to at least partially reduce the decrease over time of interfacial tension between the protein-based formulation and the lubricant.

In this second approach, the undesired interaction identified in the first aspect of the present invention can be prevented by the complex formed between the protein and the adjuvant, and the adapted protein-based formulation does not present any decrease over time of interfacial tension with the lubricant. For example, the added adjuvant may be a salt, such as an aluminum salt, for example aluminum hydroxide.

Both approaches of the second aspect of the present invention provide a simple method to reformulate a protein-based formulation that was found unstable relative to a given lubricant in a lubricated container. By using interfacial tension as a guide, expensive and lengthy stability studies may be anticipated and reduced.

A third aspect of the present invention is a method to select a lubricant adapted to a container intended to store a protein-based formulation, comprising:

a) Providing at least one lubricant to be investigated,
b) Evaluating the stability of the protein-based formulation relative to said at least one lubricant by a method according to the first aspect of the present invention,
c) Determining the sensitivity of the protein-based formulation to the interaction identified in step b),
d) Selecting a lubricant causing a non-sensitive interaction with the protein-based formulation or adapting the protein-based formulation by a method according to the second aspect of the present invention.

This method allows selecting the most adapted lubricant to a specific protein-based formulation.

More precisely, step b) allows for the identification of at least one component of the protein-based formulation that interacts with the at least one lubricant to be investigated of step a). This component is identified by comparing the decrease over time of interfacial tension between the protein-based formulation and the lubricant with the decrease over time of interfacial tension between each component of the buffer and the lubricant, according to the first aspect of the invention.

That is, this latter comparison of the decrease over time of interfacial tension between each component of the buffer and the lubricant is only necessary when all lubricants interact with the protein-based formulation. Otherwise, the lubricant which does not interact with the protein-based formulation should be chosen.

Once the component of the protein-based formulation that interacts with the lubricant has been identified according to step b), step c) further allows for the determination of the sensitivity of the protein-based formulation towards the interaction between said component and the lubricant. Then, in the case where at least one lubricant causes a non-sensitive interaction with the protein-based formulation, this lubricant is selected. In the case where all lubricants cause a sensitive interaction with the protein-based formulation, the protein-based formulation is adapted by adding an adjuvant to the formulation which brings a higher decrease over time of interfacial tension or the current investigation can be pursued with other lubricants.

Steps a) and b) are quick and inexpensive. Determining the sensitivity of a protein-based formulation to an interaction according to steps c) and d) may however require additional experiments known from the skilled person and selected according to the particular interaction under investigation. For example, if an interaction is identified between a buffer and the lubricant, a pH control may be required. However, if a limited interaction occurs with the protein, investigating the structure and folding of this interacting protein may require circular dichroism, infrared and Raman spectroscopy or nuclear magnetic resonance.

Interfacial tension is thus used as a powerful tool to investigate the stability of a protein-based formulation in a lubricated container. When an interaction is detected, interfacial tension is also a precious guide to either adapt the protein-based formulation to the lubricated container or select a lubricant compatible with the protein-based formulation.

BRIEF DESCRIPTION OF THE DRAWINGS

FIGS. 2A and 2B are concentrations of globular particles and FIGS. 2C and 2D are concentrations of non-globular particles.

FIGS. 3A and 3B are concentrations of positive particles and FIGS. 3C and 3D are concentration of negative particles.

DETAILED DESCRIPTION OF EMBODIMENTS OF THE INVENTION

In this specification, a lubricated container may be any container adapted to store a protein-based formulation and comprising a stopper and a lubricant intended to facilitate gliding of the stopper within the container. Said container may be, for example, a vial, a cartridge or a syringe. The term "protein-based formulation" is used for any prophylactic or therapeutic pharmaceutical formulation containing a peptide, a protein or a protein derivative. The word "vaccine" is used for a vaccine formulation including the vaccine protein and all adjuvants and solvents. "Vaccine protein" is used for the vaccine protein alone including the antigens and the carrier protein, but without adjuvants and solvents. "Vaccine buffer" is used for a vaccine formulation without the vaccine protein, namely only adjuvants and solvents.

Interfacial tension is defined as the tension existing at the interface between two non-miscible liquids which results from the difference in intermolecular interactions between these two liquids. In the bulk of a liquid, each molecule is equally attracted in every direction by the neighboring molecules. However, the molecules located at the interface with a non-miscible liquid will not be attracted by the molecules of the other liquid but only by their similar neighbors. This results in a tension that induces the contraction of the liquid surface to minimize the interfacial energy. The present invention uses interfacial tension as an innovative tool in the field of protein-based formulations.

A first aspect of the invention is to use interfacial tension in a method to evaluate the stability of a protein-based formulation relative to a lubricant of a lubricated container. The interest of this method has been demonstrated with two polyconjugated vaccines against meningitis, namely vaccines A and B, in the presence of commonly used silicone oil, i.e. poly-(dimethylsiloxane)—see Materials and Methods.

The following method was performed for both vaccine A and B:

In a first step, the decrease over time of interfacial tension between the vaccine buffer and silicone oil (poly-(dimethylsiloxane)) was evaluated, obtaining a Curve 1. As noted above, a vaccine buffer corresponds to the vaccine formulation without the vaccine protein.

In a second step, the decrease over time of interfacial tension between the vaccine and silicone oil was evaluated, obtaining a Curve 2.

Figure 1:
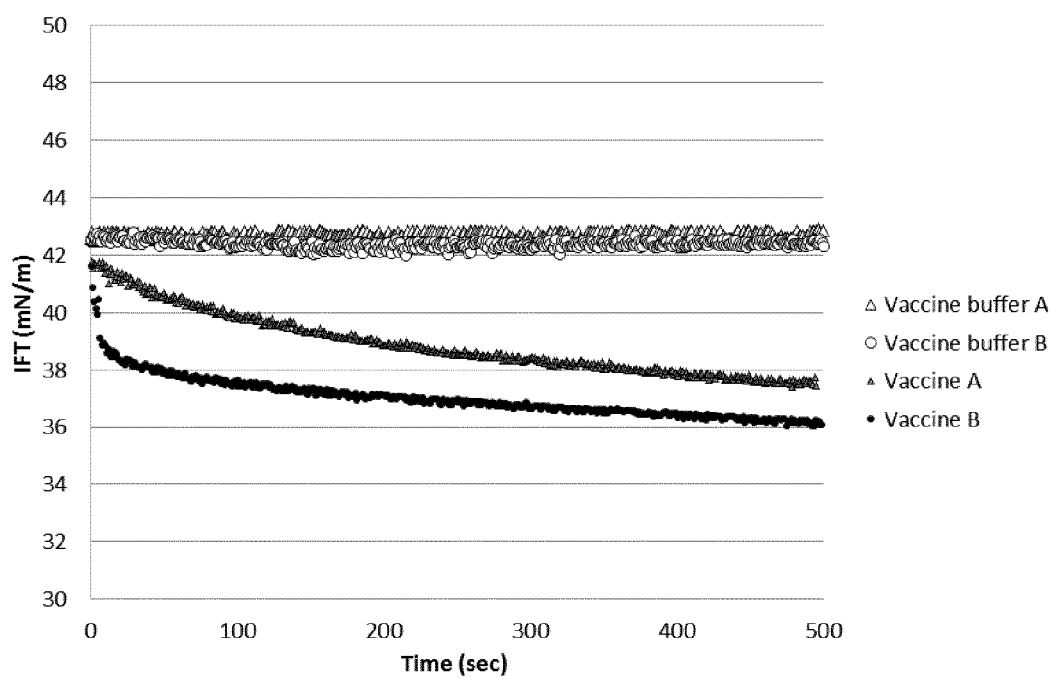
FIG. 1 is a graph showing the decrease over time of interfacial tension of two vaccines against meningitis, namely vaccine A and vaccine B and their respective buffer, namely vaccine A buffer and vaccine B buffer, which are vaccine formulations without vaccine protein.

Curves 1 and 2 were compared in a third step, for example by superimposition on the same graph, as shown in FIG. 1.

Globally speaking, as shown in FIG. 1, both vaccine A and vaccine B lead to a significant decrease over time of the interfacial tension with silicone oil. These decreases obtained with both vaccines thus demonstrate the existence of an interaction between the silicone oil and the vaccines, such an interaction leading to a stabilization of the interface and thus the reduction of the tension between the vaccine and the non-miscible silicone oil.

However, the curves obtained for vaccine A and vaccine B present two different profiles. Indeed, in the case of the vaccine A, the curve (plain triangles in FIG. 1) decreases regularly with a moderate slope leading to a reduction of the interfacial tension of about 13% (from 41.6 to 36.2 mN/m) over the duration of the experiment (i.e. 500 seconds). In contrast, the interfacial tension curve obtained with the vaccine B (plain circles in FIG. 1) shows a significant slope for the first 15 seconds and reaches a reduction of more than 20% at the end of the experiment (from 43.9 to 35.0 mN/m) over the same duration.

Now looking to the curves obtained with vaccine buffers A (void triangles in FIG. 1) and B (void circles in FIG. 1), no significant decrease over time of interfacial tension is observed, which indicates that no interaction is able to stabilize the interface which remains in a high tension state. Since a decrease of interfacial tension over time is observed with the vaccines and not with the vaccine buffers (the vaccine formulations without the vaccine proteins), it can be concluded that the vaccine proteins are responsible for the decrease over time of the interfacial tension. These results thus demonstrate a significant interaction between both vaccine proteins and silicone oil, vaccine B having a higher interaction with silicone oil than vaccine A.

Without being bound by any theory, this can be explained by a migration of the vaccine protein B to the interface with the silicone oil which leads to a quick decrease (in the first 15 seconds) of interfacial tension. Once at the interface, the protein of vaccine B may unfold in more energetic favorable conformations providing an additional decrease of the interfacial tension. Unfolded proteins may then interact with the vaccine formulation and produce protein aggregates, the interface between the silicone oil and vaccine B thus providing nucleation sites for the aggregation of vaccine proteins.

In contrast, vaccine A shows a more limited interaction with silicone oil indicating a slow migration of proteins to the interface and a limited production of protein aggregates.

This analysis is supported by the results obtained with two different analytical techniques, namely Micro-Flow Imaging (MFI™) and Resonance Mass Measurement (RMM).

MFI™ is a flow microscopic technology which captures images of suspended particles in a flowing stream. Different magnification set-points are available to suit the desired particle sizes and the image quality. The images of particles can then be further analyzed to discriminate globular particles and non-globular particles. In the present case, globular particles may be attributed to silicone particles while non-globular particles may be attributed to protein aggregates i.e. unfolded proteins aggregated together.

In this experiment, silicone oil lubricated syringes were filled respectively with vaccine A, vaccine buffer A, vaccine B and vaccine buffer B. The concentrations of globular and non-globular particles were then measured shortly after filling (T0) and after a 7-day incubation at 25° C. (T7).

Figure 2A:
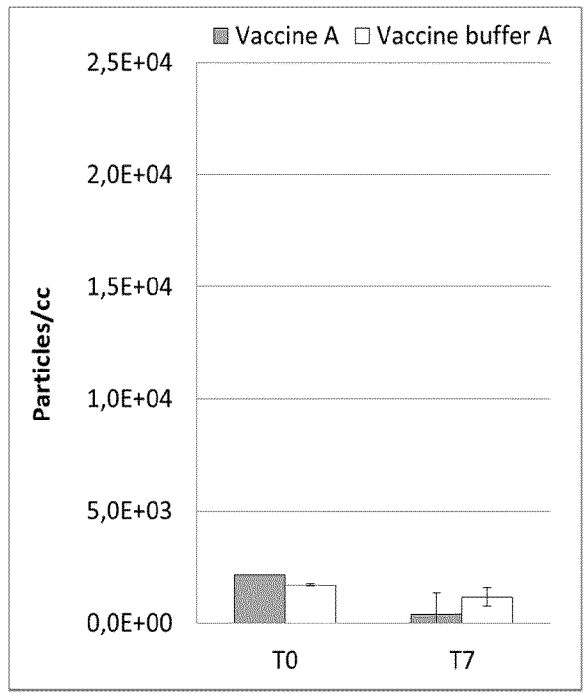
FIGS. 2A-2D are graphs showing the concentration of particles measured by Micro-Flow Imaging for respectively vaccine A, vaccine buffer A (FIGS. 2A and 2C), vaccine B and vaccine buffer B (FIGS. 2B and 2D).
Figure 2B:
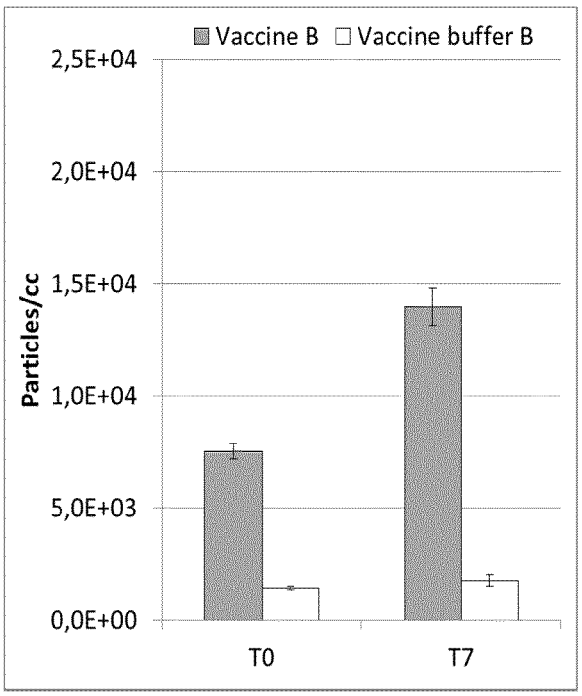
Figure 2C:
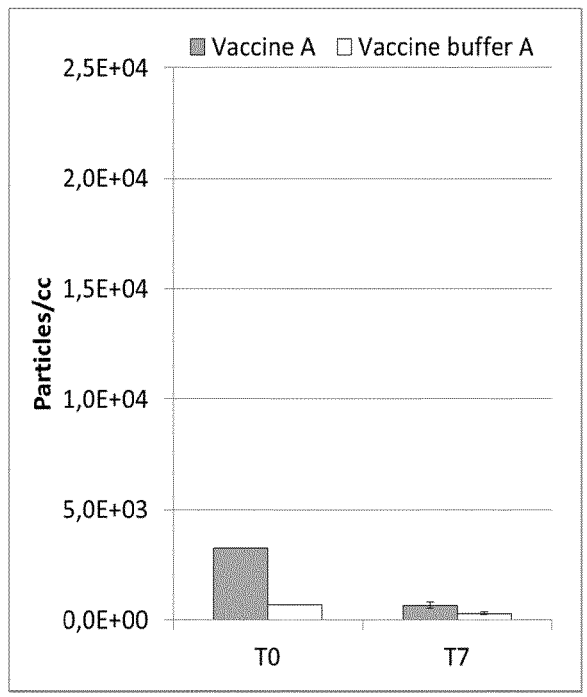
Figure 2D:
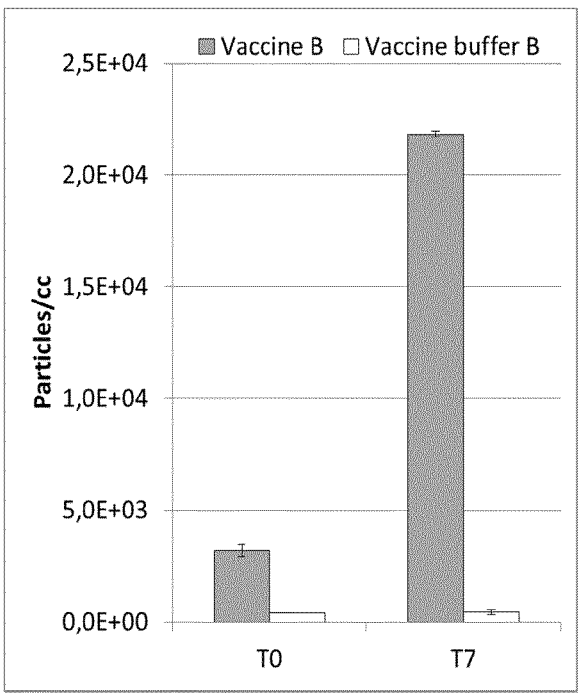

The data obtained by MFI™ are visible in FIGS. 2A-2D, where FIGS. 2A and 2B show number concentrations (particles per cubic centimeter) of globular particles and FIGS. 2C and 2D show concentrations of non-globular particles. The particle concentrations measured for vaccine A and vaccine buffer A are shown in FIGS. 2A and 2C while FIGS. 2B and 2D display the concentration measured for Vaccine B and Vaccine buffer B.

As seen on FIG. 2A the concentrations of globular particles remain at a limited value of 369 part/cc for vaccine A and 1172 part/cc for vaccine buffer A after storage. Now referring to vaccine B, a very high concentration of globular particles is visible in FIG. 2B, up to 7543 part/cc after filling and 13959 part/cc after a 7-day incubation, while vaccine buffer B produced particle concentrations below 1800 part/cc.

A similar result is obtained with non-globular particles, attributed to protein aggregates, as seen in FIGS. 2C and 2D. Indeed, limited concentrations of 673 particles per cc for the lubricated syringes filled with vaccine A and 283 part/cc for vaccine buffer A were measured after 7 days (FIG. 2C), but a very high concentration of non-globular particles was reached in the lubricated syringes filled with vaccine B (FIG. 2D), above 21 000 part/cc after 7 days. Once again, vaccine buffer B only produces a limited amount of 444 part/cc of non-globular particles when incubated 7 days in a lubricated container.

These results demonstrate a strong interaction between the vaccine B protein and the silicone oil, in accordance with results obtained with the method according to the first aspect of the invention, based on the decrease of the interfacial tension.

In addition to MFI™, data have been collected by using Resonance Mass Measurement (RMM). RMM is based on a vibrating microfluidic circuit allowing the determination of the number and size of particles circulating through it, by measuring the vibration frequency shift. This experiment allows measuring particles of smaller size than MFI™ as well as discriminating silicone oil droplets from proteins aggregates, as the vibration frequency shift depends on the particles mass. Consequently, particles having a lower density than the analysis medium (the corresponding vaccine buffer in this experiment) give a positive shift and may be attributed to silicone oil. In contrast, particles having a higher density than the analysis medium give a negative shift and may be attributed to protein aggregates.

Figure 3A:
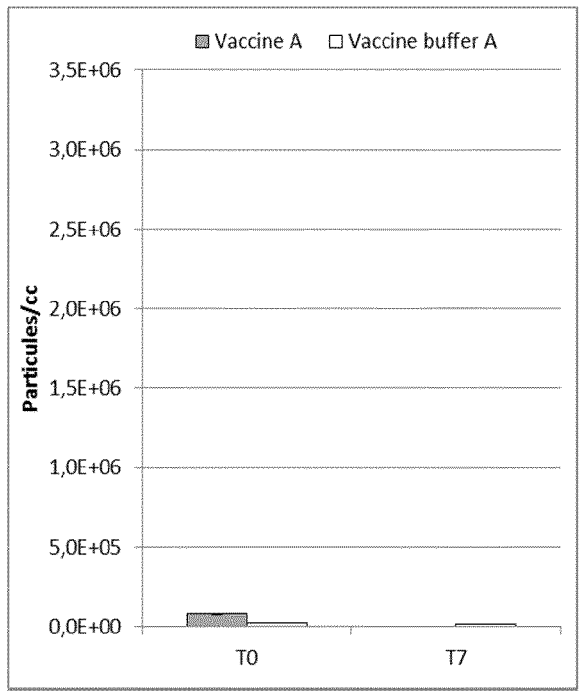
FIGS. 3A-3D are graphs showing the concentration of particles measured by Resonance Mass Measurement for respectively vaccine A, vaccine buffer A (FIGS. 3A and 3C), vaccine B and vaccine buffer B (FIGS. 3B and 3D).
Figure 3B:
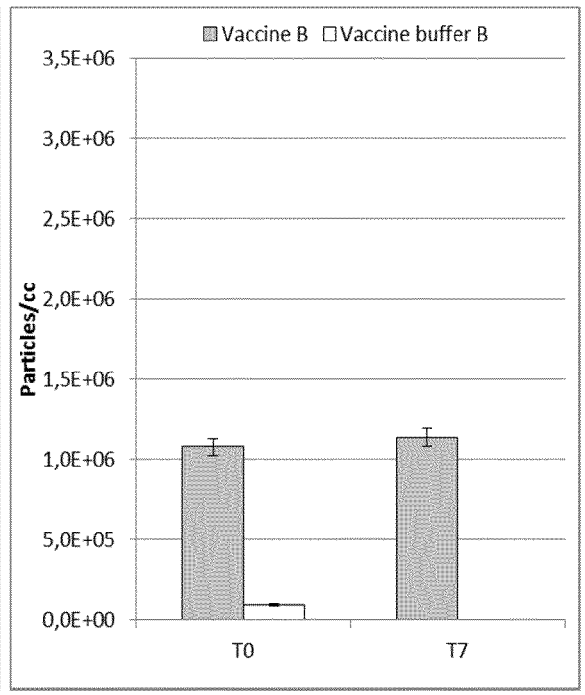
Figure 3C:
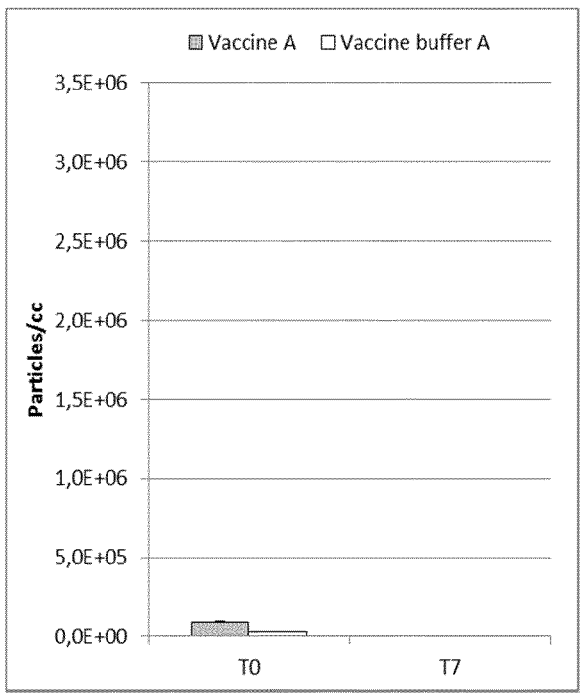
Figure 3D:
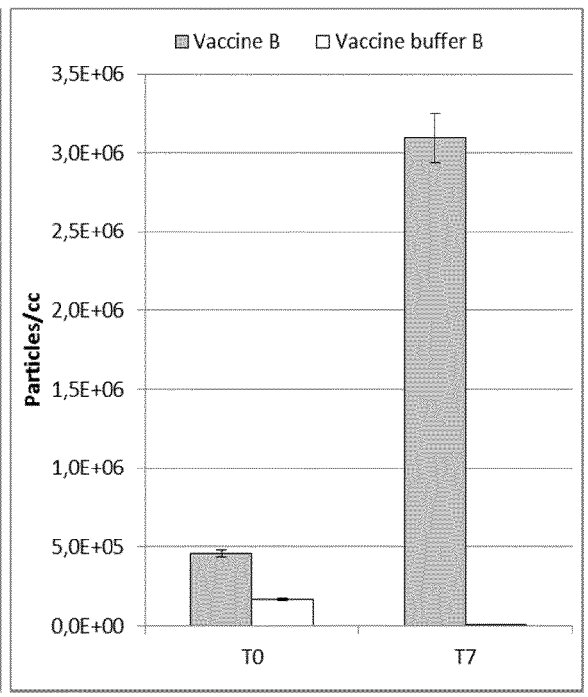

The results of these experiments are visible in FIGS. 3A-3D: FIGS. 3A and 3B correspond to the concentration of positive particles, while FIGS. 3C and 3D provide concentration on the negative particles. The data obtained show low concentrations of positive particles of 79,933 part/cc (attributed to silicone oil) for vaccine A and 25,867 part/cc for vaccine buffer A, after mixing (T0) and even lower concentration after a 7-day storage (T7, see FIG. 3A). In contrast, as seen in FIG. 3B, vaccine B produces a high concentration of positive particles (above $1 \times 10^6$ particles per cc) during incubation in a lubricated container, while the buffer of vaccines A or B does not produce a significant particles concentration, below 95,000 part/cc. Now looking to the measurements of negative particles, attributed to protein aggregates (FIGS. 3C and 3D): vaccine A and vaccine buffer A do not produce significant concentration of particles, below 100,000 part/cc as well as vaccine buffer B below 170,000 part/cc. On the contrary, lubricated syringes filled with vaccine B produce a significant concentration of more than 460,000 negative particles per cubic centimeter after mixing (T0), this concentration showing after seven days (T7) a dramatic rise superior to 600% by reaching $3.1 \times 10^6$ particles per cc.

It is thus possible to conclude from these different experiments that a significant interaction between vaccine B and silicone oil occurs. This interaction can be attributed to the nature of the vaccine protein present in vaccine B as vaccine buffer B does not produce a significant concentration of particles in presence of silicone oil.

The results of both MFI™ and RMM experiments therefore provide a strong support to the conclusion obtained by the method according to the present invention with the interfacial tension measurement: the vaccine B is incompatible with silicone oil, and either the vaccine B formulation or the silicone oil as a lubricant should be changed in order to deliver stable vaccine B into a prefilled container lubricated with silicone oil. This also validates interfacial tension as a fast and powerful tool to obtain an insight of the stability of a protein-based formulation in a lubricated container. Indeed, the decrease over time of the interfacial tension between a lubricant and a protein-based formulation such as a vaccine is correlated with a low stability and the generation of a strong concentration of protein aggregates.

Regarding particles attributed to silicone oil, the different results observed between the moderate concentration of globular particles measured by MFI™ and the high concentration of positive particles measured by RMM may be linked with the different particle sizes observed by these techniques. In particular, MFI™ observes particles having diameters ranging from 1 to 100 microns while RMM detects particles of diameters ranging from 0.05 to 5.00 microns. It is also known that Polysorbate 80 is able to stabilize air bubbles in the form of small size particles, effectively observed by RMM in the form of positive particles.

In the examples of vaccines A and B, only the time dependence of the interfacial tension between the vaccine buffer and the lubricant were evaluated in the first step of the method, since an interaction occurred between the lubricant and vaccines protein. However, other components of the buffer may interact with the silicone oil, such a case leading to evaluate the decrease over time of the interfacial tension between the components of the formulation and the lubricant in order to identify, in the third step, which components are responsible for the interaction. Indeed, some components of the buffer may also produce a strong interaction with the lubricant, resulting in the production of particles, the degradation of the therapeutic protein or at least the destabilization of the protein-based formulation.

Figure 4:
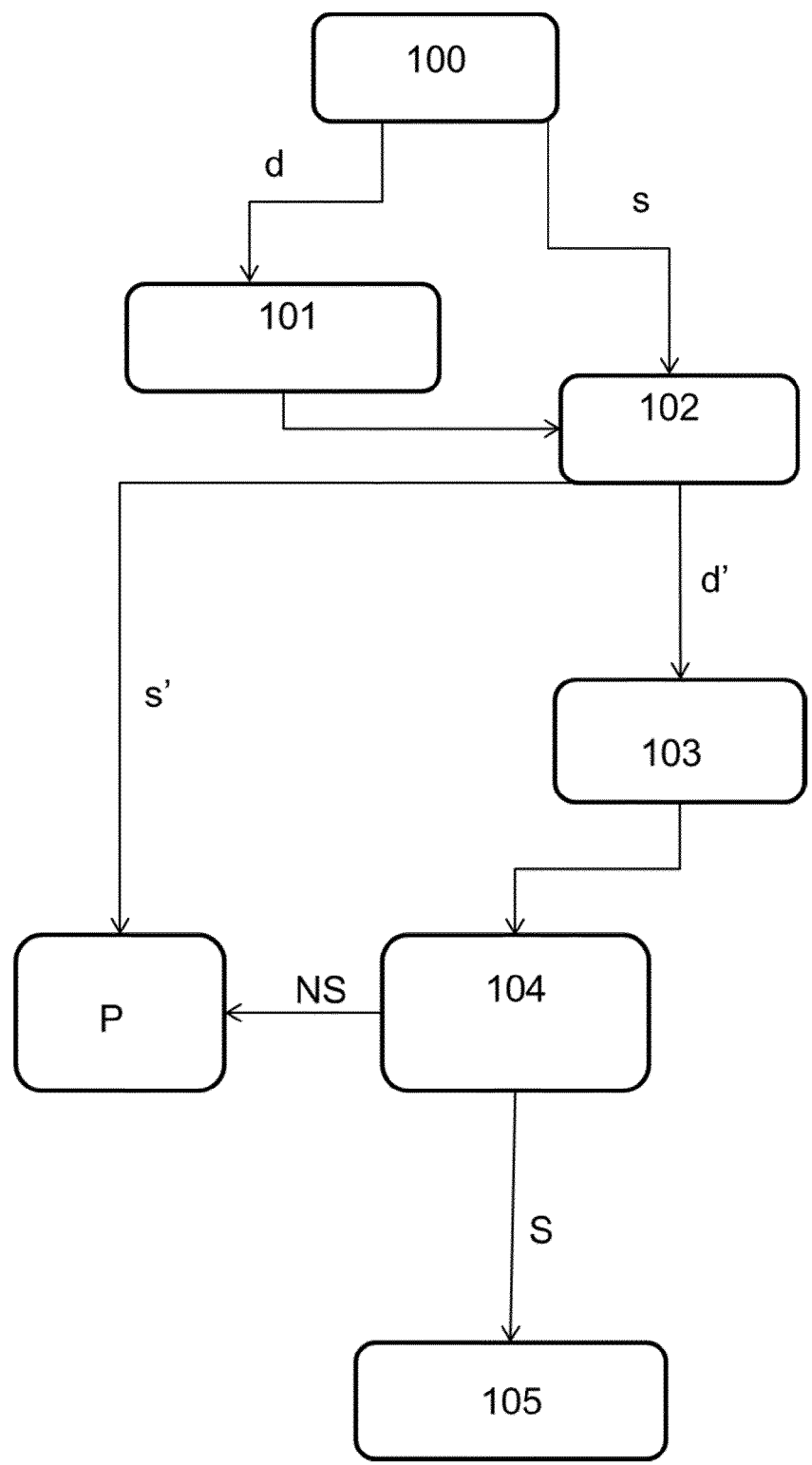
FIG. 4 is a flow chart summarizing the method according to the first aspect of the present invention.

The flow chart presented in FIG. 4 sums-up the different steps of a general method to evaluate the stability of any protein-based formulation relative to a lubricant of a lubricated container. In step 100, the interfacial tension between the buffer and the lubricant is evaluated.

For example, if the interfacial tension between the buffer and the lubricant is decreasing over time in the first step of the method (branch d), therefore an intermediate step 101 is required to evaluate the interfacial tension between each component of the formulation buffer and the lubricant. Alternatively, if the interfacial tension between the buffer and the lubricant is found to be stable (branch s), the second step 102 can be carried out directly. In said second step 102 of the method, the interfacial tension between the protein-based formulation and the lubricant is evaluated. If stability is found in this step, it could be concluded that the protein-based formulation is stable in the studied lubricated container (branch s') and the next development phase P can be conducted.

However, if any interaction is detected by a decrease of the interfacial tension (branch d'), it is then required to identify which component actually interacts in a third step 103 of the present method. This allows, in a fourth step 104, investigating the sensitivity of the protein-based formulation towards the interaction identified in the third step. Indeed, a limited interaction of a component of the formulation with the lubricant may be acceptable, for example if this component is introduced in a significant concentration and/or if its function is not impeded by the interaction. Other experiments may thus be required to determine if the interaction actually affects the stability or the potency of the protein-based formulation. For example, if an interaction between a pH buffering agent and the lubricant is identified in the third step 103 of the method, it may be required to check the pH of the protein-based formulation after aging, to ascertain that the protein-based formulation is still at the required pH. Similarly, if an oxygen scavenger is found to interact with the lubricant, it may be required to investigate the protein oxidation after aging, as oxygen may compete with the lubricant and cancel the interaction with the scavenger. In the case where the protein-based formulation is not sensitive to the interaction (branch NS), it may then be possible to proceed with the next development step P of the protein-based formulation. However, if the protein-based formulation is found sensitive to the particular interaction (branch S), an adaptation of the protein-based formulation or of the lubricant might be required (step 105).

Generally speaking, an interaction between the protein and some critical components, such as squalene in the case of an emulsion-adjuvanted vaccine, may not require additional experiments as the high sensitivity of the protein-based formulation to these interactions is obvious or well documented. In these cases, it may be required to adapt the protein-based formulation or the lubricant, without determining the sensitivity of the protein-based formulation, in the optional fourth step 104.

According to a second aspect of the invention, interfacial tension is used in a method to adapt a protein-based formulation to a lubricated container. As previously noted, a way to overcome this incompatibility between a protein-based formulation and a lubricant may be to adapt the protein-based formulation in order to prevent the non-desired interaction determined in the method according to the first aspect of the invention.

Adapting a protein-based formulation to a lubricated container may be achieved by the addition of a formulation component realizing a competing interaction, i.e. either kinetically or thermodynamically more favorable than the interaction between the identified interacting component and the lubricant. The competing interaction may either occur between the additional component and the lubricant or between the additional component and the protein-based formulation.

A first approach is thus to prevent the interaction between the protein-based formulation and the lubricant by creating a stronger competitive interaction between an additional component of the buffer and the lubricant. This additional component may be a new component to the protein-based formulation or an already present component, provided that the component concentration may be significantly changed without affecting the stability of the protein-based formulation.

This first approach has been investigated by the applicant in the example of vaccine B. Indeed, the method according to the first aspect of the invention demonstrated an incompatibility between the vaccine B protein and silicone oil. However, vaccine B comprises Polysorbate 80 as a non-ionic surfactant (see Materials and Methods) and this component is able to compete with the vaccine B protein in the interaction with silicone oil.

To determine the appropriate concentration of Polysorbate 80, the decrease over time of the interfacial tension between different concentrations of Polysorbate 80 and silicone oil has been evaluated and compared to the decrease produced by vaccine B.

Figure 5:
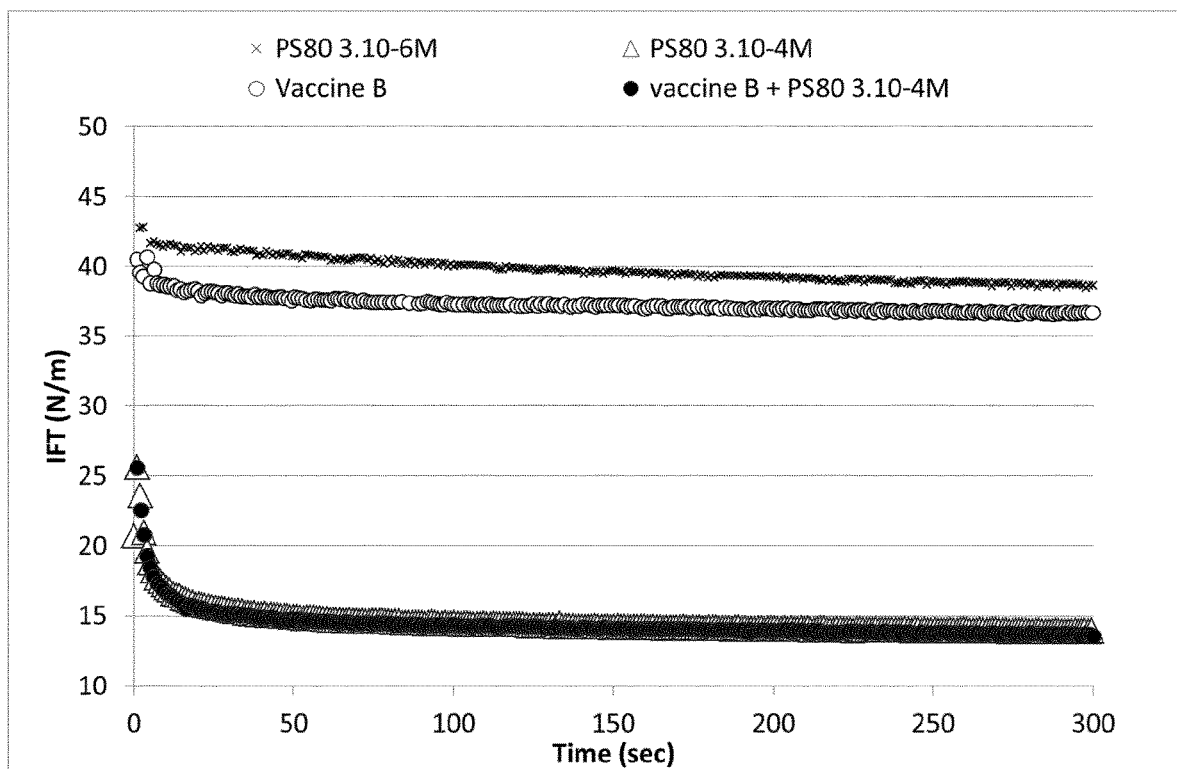
FIG. 5 is a graph showing the decrease over time of interfacial tension between silicon oil and respectively Polysorbate 80 at a concentration of $3 \times 10^{-6}$ M (cross), Polysorbate 80 at a concentration of $3 \times 10^{-4}$ M (triangles), vaccine B (void circles) and vaccine B with Polysorbate 80 at a concentration of $3 \times 10^{-4}$ M (plain circles).

In FIG. 5, the decrease over time of the interfacial tension between Polysorbate 80 in concentrations of $3 \times 10^{-6}$ M and $3 \times 10^{-4}$ M and silicone oil is superimposed with the decrease of the interfacial tension between vaccine B and silicone oil. If a concentration of Polysorbate 80 of $3 \times 10^{-6}$ M only produces a limited decrease from 41 to 36 mN/m, a concentration of $3 \times 10^{-4}$ M produces a dramatic decrease of interfacial tension reaching a minimum of 14 mN/m, well below the minimum obtained by Vaccine B at 36 mN/m. This result indicates that vaccine B may be adapted to be stable with silicone oil by setting the concentration of Polysorbate 80 at $3 \times 10^{-4}$ M. This adapted formulation is then referred as vaccine B+PS80 for the next studies and the corresponding buffer as vaccine B buffer+PS80.

The stability of vaccine B+PS80 has then been assessed with experiments of Micro-Flow Imaging (MFI™) and Resonance Mass Measurement (RMM).

Figure 6A:
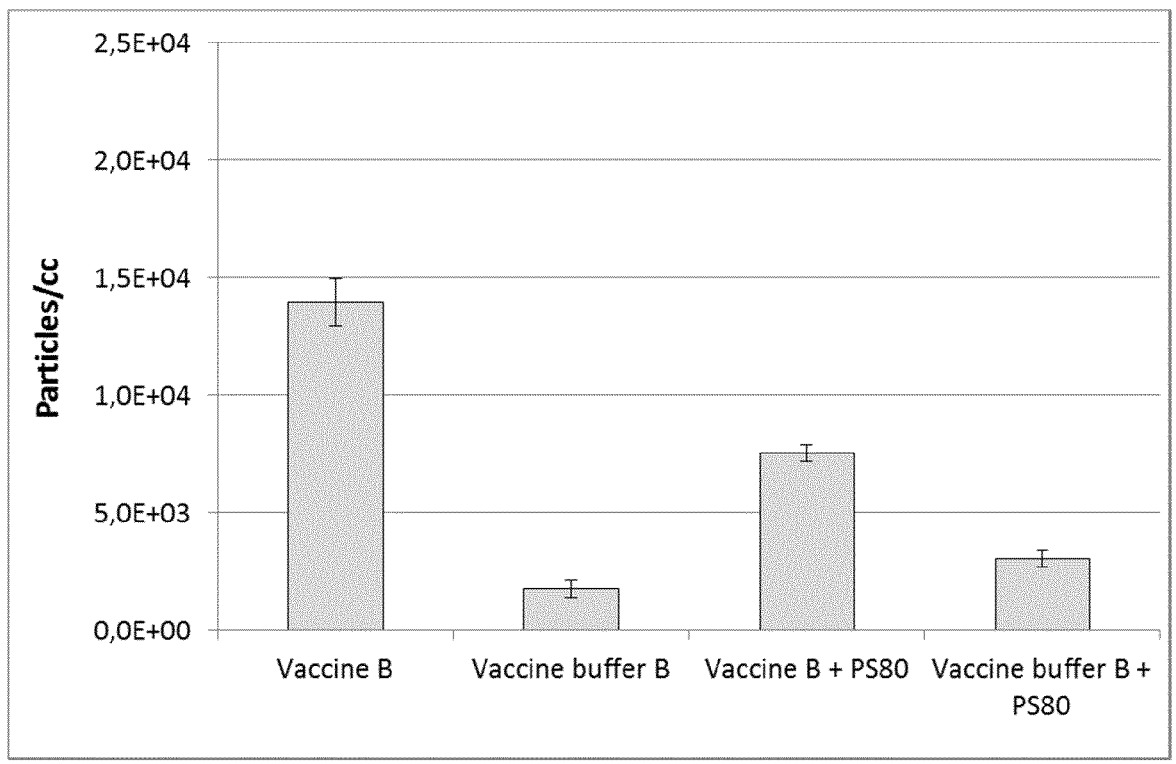
FIGS. 6A and 6B are graphs showing the concentration of particles measured by Micro-Flow Imaging for respectively vaccine B, vaccine buffer B, vaccine B with Polysorbate 80 at a concentration of $3 \times 10^{-4}$ M and vaccine buffer B with Polysorbate 80 at a concentration of $3 \times 10^{-4}$ M.
Figure 6B:
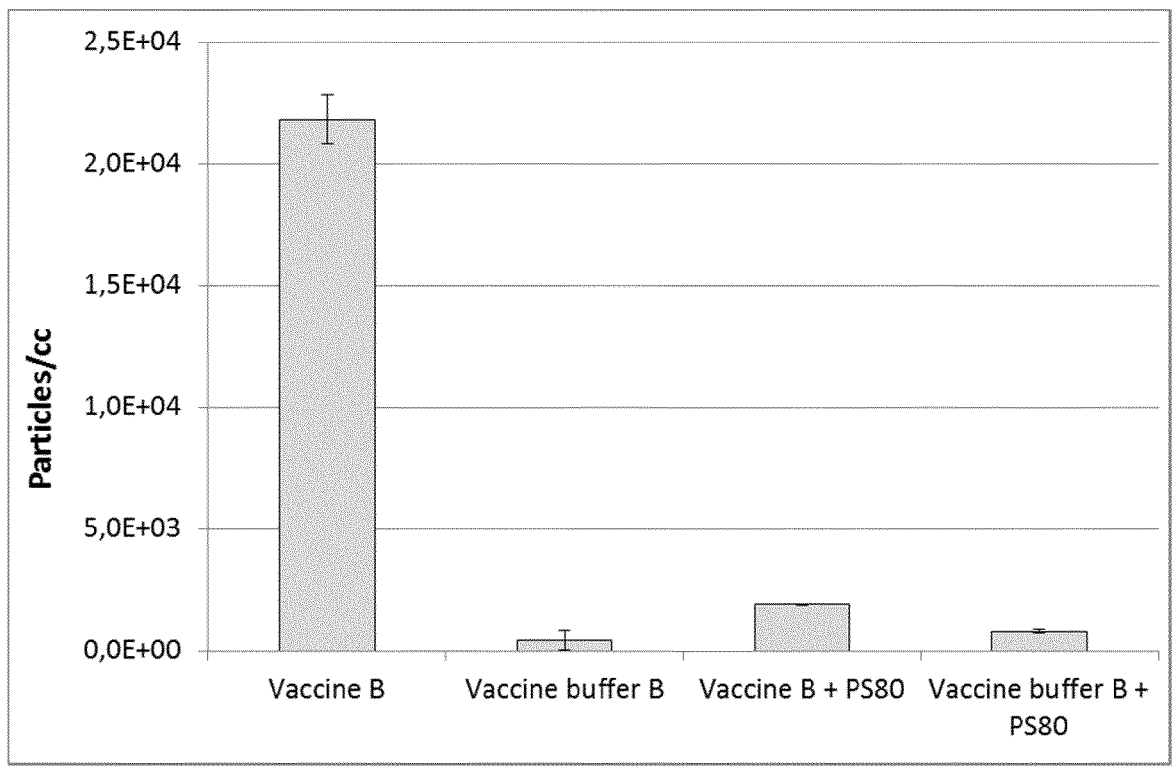

FIGS. 6A and 6B show the concentration of particles produced by vaccine B and vaccine B+PS80 measured by MFI™ as well as the concentration of particles for vaccine B buffer and vaccine buffer B+PS80, all after seven days of incubation in a syringe lubricated with silicone oil. FIG. 6A present the concentration of globular particles (attributed to silicone oil) while FIG. 6B present the concentration of non-globular particles (attributed to protein aggregates) In this experiment, the concentration of globular particles (FIG. 6A) produced by the adapted formulation, namely vaccine B+PS80, was found to be nearly half of the concentration produced by the original formulation (vaccine B), from 13959 to 7533 part/cc. Regarding the non-globular particles, attributed to protein aggregates (see FIG. 6B), the modified formulation vaccine B+PS80 only produces a concentration of 1887 part/cc which is about 9% of the concentration of 21826 part/cc produced by vaccine B.

Figure 7A:
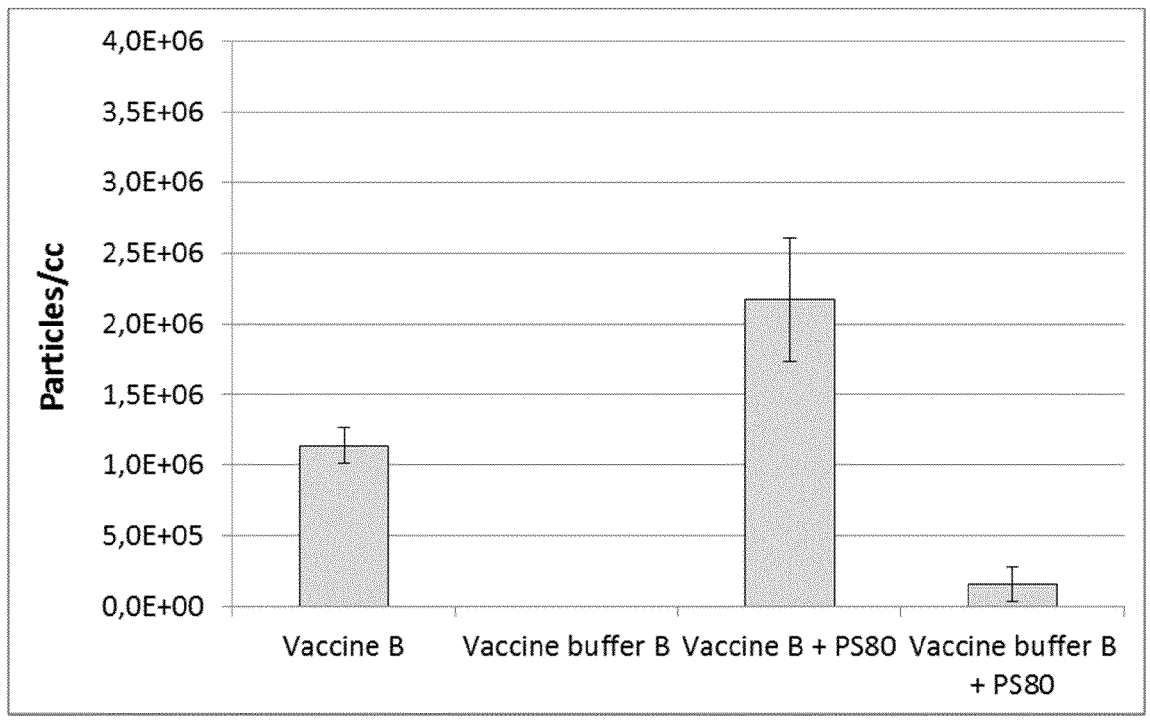
FIGS. 7A and 7B are graphs showing the concentration of particles measured by Resonance Mass Measurement for respectively vaccine B, vaccine buffer B, vaccine B with Polysorbate 80 at a concentration of $3 \times 10^{-4}$ M and vaccine buffer B with Polysorbate 80 at a concentration of $3 \times 10^{-4}$ M.
Figure 7B:
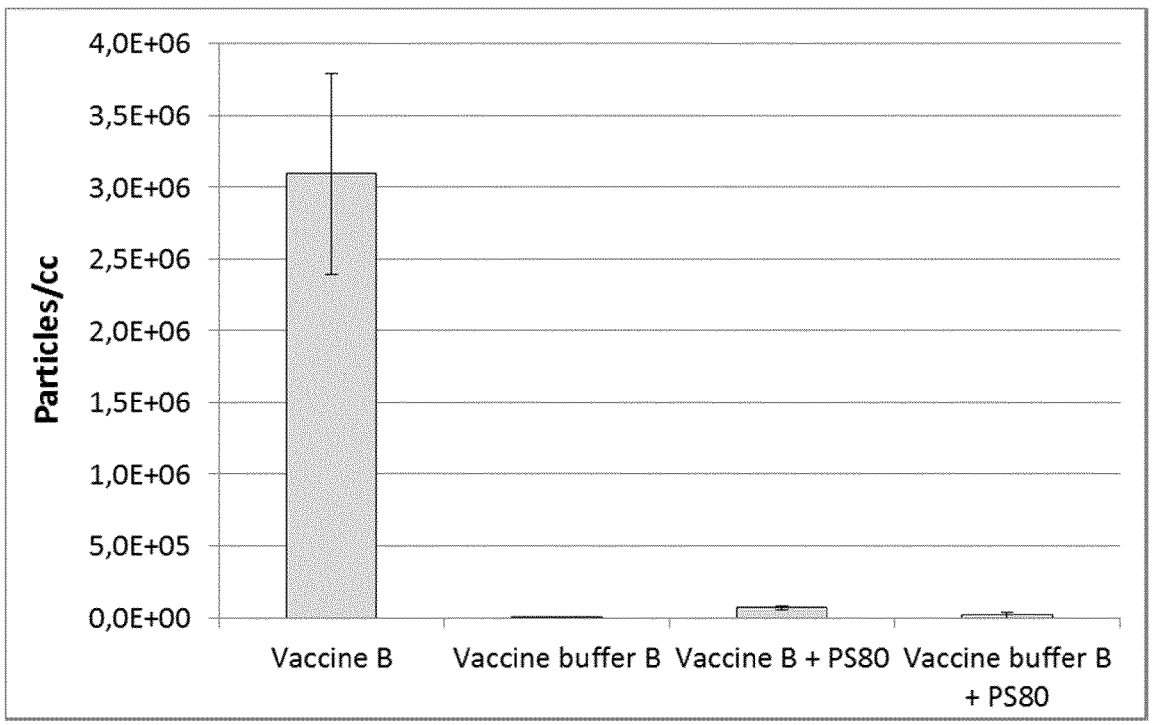
Figure 8:
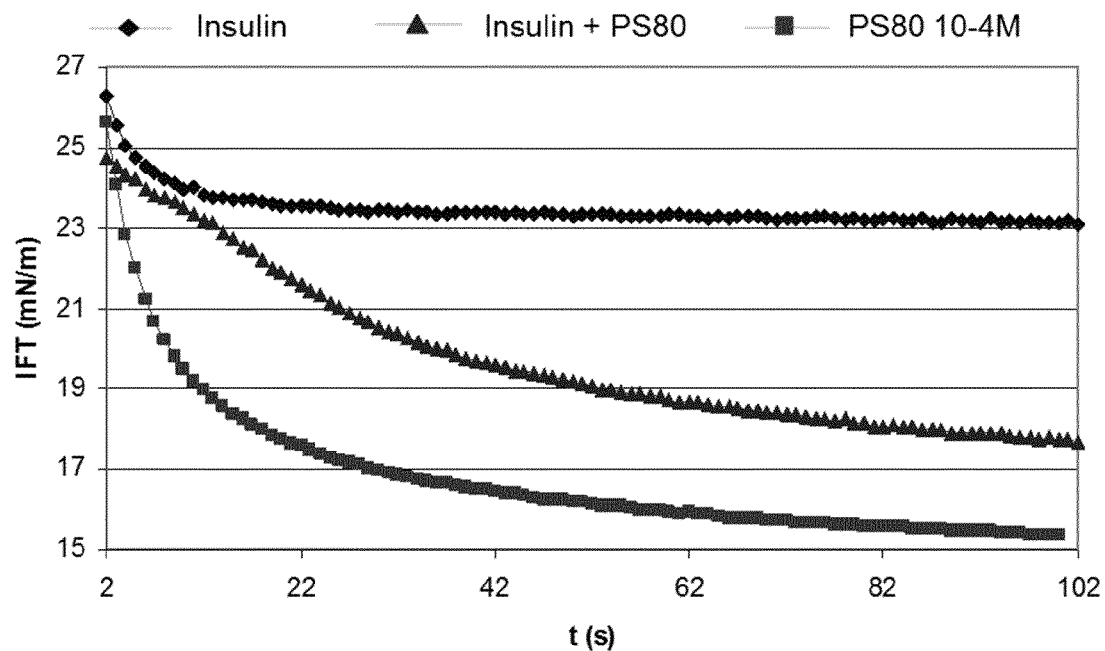
FIG. 8 is a graph showing the decrease of interfacial tension over time between silicone oil and, respectively, insulin at a concentration of 1 g/l, Polysorbate 80 at a concentration of $10^{-4}$ M (diamonds), Polysorbate 80 at a concentration of $3 \times 10^{-4}$ M (triangles) and insulin adapted with Polysorbate 80 at a concentration of $10^{-4}$ M (squares).
Figure 9:
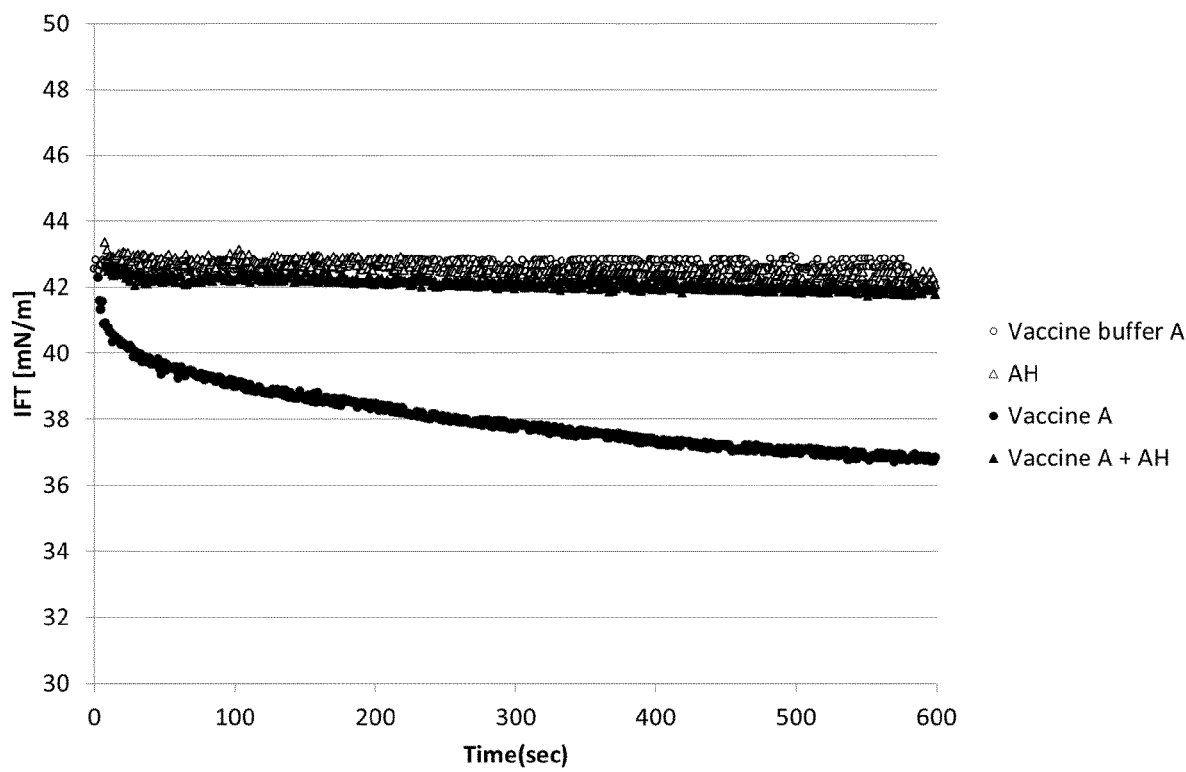
FIG. 9 is a graph showing the decrease of interfacial tension over time between silicone oil and respectively vaccine buffer A (void circles), aluminum hydroxide (void triangles), vaccine A (plain circles) and vaccine with aluminum hydroxide (plain circles).
Figure 10:
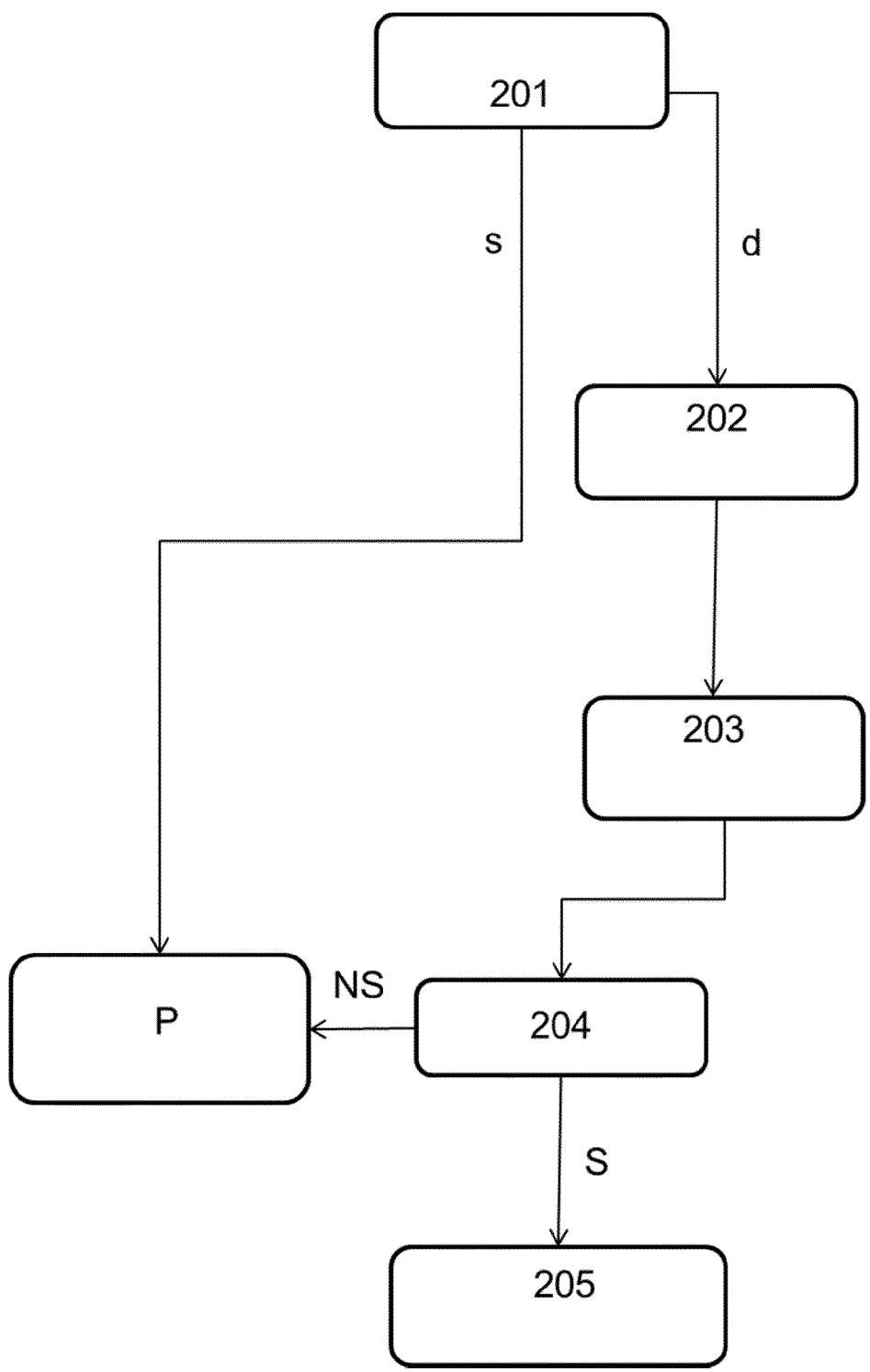
FIG. 10 is a flow chart summarizing the method according to the third aspect of the present invention.

The RMM results are shown in FIGS. 7A and 7B, where FIG. 7A shows the concentration of positive particles (attributed to silicone particles) and FIG. 7B the concentration of negative particles (attributed to protein aggregates). After 7 days of incubation, the adapted formulation (vaccine B+PS80) produces a higher concentration of positive particles than vaccine B, above $2 \times 10^6$ part/cc. However, the concentration of negative particles produced by vaccine B+PS80 is reduced to 72667 part/cc which is about 3.3% of the concentration produced by vaccine B.

These experimental results provide support for a strong reduction of the interaction between Vaccine B and the silicone oil lubricant after the addition of Polysorbate 80, according to the method of the second aspect of the invention. Polysorbate 80 successfully competes with Vaccine protein B in the interaction with the protein, the interaction between vaccine protein B and silicone oil being efficiently prevented by Polysorbate 80. This method thus allows the adaptation of a protein-based formulation to a given lubricant and in this case allows the safe storage of vaccine B in a lubricated container such as a prefilled syringe. Although Polysorbate 80 has been used to adapt vaccine B, other non-ionic surfactant may be appropriate, as long as they are compatible with the protein and the other components of the formulation.

A similar approach has been investigated with insulin, which is another common protein-based formulation.

Now referring to FIG. 8, the decrease over time of interfacial tension between an insulin formulation and silicone oil demonstrate a significant interaction. The insulin formulation was successfully adapted to silicone oil by the addition of Polysorbate 80 at a concentration of $1\times10^{-4}$ M and is referred as "insulin+PS80" in FIG. 8. Insulin+PS80 produces a greater decrease over time of the interfacial tension with silicone oil, down to 17 mN/m, than the decrease observed with the original insulin formulation (23 mN/m at 100 s). However, the superimposition of the interfacial tension curves of Polysorbate 80 and the adapted insulin formulation allows concluding that only the Polysorbate 80 interacts with silicone oil, the undesired interaction with insulin being efficiently masked.

A second approach investigated by the applicant was to add an additional component interacting with the protein of an unstable protein-based formulation. Indeed, the net charge of the vaccine A protein is negative and a complex may be formed with aluminum cations. Vaccine A has thus been adapted by introducing 2 g/dm$^3$ of aluminum hydroxide, the adapted formulation being referred as "vaccine A+AH".

FIG. 9 traces the decrease over time of interfacial tension between silicone oil and respectively vaccine buffer A, vaccine A and vaccine A+AH (the adapted formulation). While a decrease of the interfacial tension from 43 to 36 mN/m is shown between vaccine A and silicone oil as a result of the previously demonstrated interaction as previously, vaccine A+AH only produces a limited decrease of the interfacial tension to 42 mN/m. This decrease is similar to the decrease produced by vaccine buffer A over the same duration. It is therefore deducted that vaccine A+AH, stored in a container lubricated with silicone oil, will produced a limited concentration of particles, similarly to what is obtained for vaccine buffer A and shown in FIGS. 2A, 2C, 3A, 3C. Contrarily to the first approach where Polysorbate 80 successfully competed with vaccine protein B to interact with silicone oil, the interaction between vaccine protein A and silicone oil in this second approach has been prevented by forming a vaccine protein complex. Such a vaccine protein complex is not able to interact with silicon oil anymore and vaccine A+AH is as stable as vaccine buffer A. This result therefore supports an efficient adaptation of vaccine A by the addition of a complexing salt. Aluminum hydroxide has been used in the example below but other salt such as aluminum phosphate may have been chosen.

According to a third aspect of the invention, interfacial tension is used in a method to select a lubricant adapted to a container intended to store a protein-based formulation.

Referring to FIG. 10, the decrease over time of interfacial tension between the protein-based formulation and each investigated lubricant is evaluated in a first step 201. If a lubricant does not produce a significant decrease i.e. does not produce any interaction with the protein-based formulation is identified (branch s), it is then possible to select it and to proceed with the next phase P of the formulation process.

However, if all lubricants interact with the protein-based formulation (branch d), the decrease over time of interfacial tension between each component of the buffer and each investigated lubricant has to be evaluated in a second step 202. This step allows determining in a third step 203 which component(s) of the protein-based formulation actually interact with which lubricants. In this step a lubricant not interacting with the protein of the protein-based formulation may be selected for further investigation, while a lubricant interacting with the protein may be disqualified.

With these data, one can determine in a fourth step 204 if the protein-based formulation is sensitive to the interaction with the selected lubricant by conducting additional experiments. These experiments can involve particle counting methods such as MFI™ or RMM (Resonance Mass Measurement), structural techniques such as nuclear magnetic resonance or circular dichroism and other techniques such liquid chromatography, size-exclusion chromatography, pH-metry, immuno-assays or in-vivo experiments, depending on the component of the protein-based formulation that interacts with the lubricant. Indeed, some interactions might be found acceptable as not impeding the potency or the stability of the protein-based formulation. If a lubricant producing a non-sensitive interaction with the protein-based formulation is found in this fourth step 204 (branch NS), it can be selected before proceeding to the next development step P of the protein-based formulation. However, if all lubricants produce sensitive interactions with the protein-based formulation (branch S), it may be required, in a fifth step 205, either to adapt the protein-based formulation as described in the second aspect of the present invention or to pursue the current investigation with other lubricants.

Materials and Methods

Solutions

The methods of the present invention were investigated with two different polyconjugated meningitis vaccines, namely vaccine A and vaccine B, both containing only one serotype. These vaccines were purchased on the market. Vaccine A buffer contained 7 mg/ml of NaCl, 0.184 mg/ml of $NaH_2PO_4.H_2O$, 0.96 mg/ml of $Na_2HPO_4.7H_2O$ and 14.6 mg/ml of mannitol. Vaccine B buffer contained 9 mg/ml of NaCl; 1.335 mg/ml of $Na_2HPO_4.2H_2O$; 0.345 mg/ml of $NaH_2PO_4.H_2O$, 0.68 mg/ml of $KH_2PO_4$ and 25 mg/ml of sucrose. All chemical compounds were purchased from Sigma-Aldrich. Aluminum Hydroxide (AH) solution was supplied in the purchased vaccine A kit, in concentration of 2 mg/ml and was thus compliant with the USP and EP grade.

Polyoxyethylene sorbitan monooleate, referred as Polysorbate 80 or PS80 was purchased as molecular biology grade from Sigma-Aldrich under the brand name TWEEN® 80. PS80 solutions were prepared with a final concentration of $3 \times 10^{-4}$ M, $3 \times 10^{-5}$ M and $3 \times 10^{-6}$ M respectively. Vaccine B+PS80 was prepared with a final concentration of PS 80 of $3 \times 10^{-4}$ M.

Silicon oil was a medical grade poly-(dimethylsiloxane) (PDMS) purchased from Dow Corning under the name DC 360. Both 20 cSt and 1000 cSt were investigated in a preliminary study and identical interfacial tension curves were obtained with air or phosphate buffer solution, respectively. Consequently, the less viscous 20 cSt PDMS, giving a larger drop curvature was used for interfacial tension measurements (see material and methods of interfacial tension measurements).

Interfacial Tension Measurements

The decrease over time of the interfacial tension was measured using a Profile Analysis Tensiometer (PAT-1M tensiometer, SINTERFACE Technologies, Berlin, Germany) based on the pendant drop technique. The PAT-1M tensiometer generates droplets in air or liquid with a controlled dosing system, the drop formation being captured by a high definition video camera. The Sinterface PAT-1M tensiometer software allows the image acquisition, the edge detection, and use the Young-Laplace equation to determine the interfacial tension. The temperature of the measurement into the 20-ml glass cell was controlled to be 25° C.±2° C. The cell was closed by a lid with an immersed poly-(tetrafluoroethylene) (PTFE) capillary having an external diameter of 1.0 mm. A drop of the studied solution was formed at the immersed end of the capillary. In the present methods, a drop of vaccine, vaccine buffer or modified formulation was formed into the PDMS (20 cSt) environment. The surface area of the drop was controlled to be constant during the whole experiment by an automatic regulation. The volume added to the drop during the experiment was also continuously monitored. The drop surfaces were adjusted for each experiment to allow monitoring of the drop curvature, in agreement with the Young-Laplace equation. As a result, a drop surface of 70 mm² was used for solution having no PS80 or PS80 below the CMC ($1 \times 10^{-5}$ M), and 40 mm² for other solutions.

Stability Study

The stability of vaccine A and vaccine B formulations in lubricated containers was investigated in order to confirm correlation with the interfacial tension measurements. The containers were glass syringes (Hypak™, 29G½, RNS BD260 Black, Ultra low tungsten, BD—Pharmaceutical Systems, Le Pont-de-Claix, France) lubricated with 0.4 mg silicone with a diving nozzle. All syringes were stoppered with Hypak SCF 1 mL non-lubricated coated stoppers.

Syringes were filled with the appropriate solution (vaccine or buffer) and were stored in a vertical position (tip on top) at a temperature of 25° C.±2° C. and a humidity of 60% RH±5%. Syringes were opened by a careful removal of the plunger stopper and the solution transfer of the solution from the flange into clean glassware. Particle counting was performed on a MicroFluid Imagine™ (MFI™) and via Archimedes Resonance Mass Measurement (RMM) equipment a short time after filling and after a 7-day storage.

Particles Counting Methods Used During the Stability Study

In order to estimate the concentration and size of the particles created during the stability study, a MFI™-DPA5200 Series A of Brightwell Technologies and a Resonant Mass Measurement (RMM) via Archimedes system (Affinity Biosensors, Santa Barbara, Calif.) were employed.

The MFI™-5200 instrument was equipped with a 100 μm flow cell, operated at high magnification. MFI™ View software MVSS version 2.R3 and MVAS version 1 (Protein-Simple) was used for data analysis. The equipment was initially calibrated using the 10 μm polystyrene NIST traceable particle size standards (Duke Scientific Corp. Fremont, Calif.). Prior to each sample run, particle-free fluid was flushed through the system to provide a clean baseline and to optimize the illumination. The samples were then gently inserted in the flow cell using a peristaltic pump. Three individual runs with 0.5 ml running volumes were performed. Customer filters where built thanks to the MVAS software of the MFI™ system. In agreement with Sharma et al, PharmTech 2009 (33), p. 74-9, silicone-oil droplets have a consistently higher aspect ratio compared with aggregated protein particles of the same size, which support usage of a simple software filter with an aspect ratio (AR) >0.85 cutoff. This filter separates globular from non-globular populations and captured of about 95-98% of particles with visually fibril morphology.

The Archimedes system was equipped with a Hi-Q Micro Sensor (Affinity Biosensors) and controlled by ParticleLab software version 1.8. The sensor was flushed for 60 s with purified water before the analysis. Subsequently, possible impurities in the system were removed by at least five "sneeze" operations (liquid in the sensor is pushed into both directions) and the system was flushed again for 60 s with purified water. The sample solution was then loaded for 45 s as described by D. Weinbuch et al., Journal of Pharmaceutical Sciences 2013 (102), p. 2152-65. The analysis was set up for the period of 10 min. A fresh sample solution was loaded for each of the triplicate measurements. Size determination and sorting of particles by RMM is based on the frequency shift and explained in P. Dextras et al, Analytical Chemistry 2009 (81), p. 4517-23.

The invention claimed is:

1. A method to evaluate the stability of a protein-based formulation comprising a protein, a peptide and/or a protein derivative and a buffer relative to a lubricant of a lubricated container in which said formulation is intended to be stored, the method comprising:
    a) preparing a first solution comprising the buffer and the lubricant;
    b) evaluating a decrease over time of interfacial tension between the buffer and the lubricant in the first solution;
    c) preparing a second solution comprising the protein-based formulation and the lubricant;
    d) evaluating a decrease over time of interfacial tension between the protein-based formulation and the lubricant in the second solution; and
    e) identifying at least one component of the protein-based formulation exhibiting an interaction with the lubricant by comparing the decrease evaluated in step d) with the decrease evaluated in step b).

2. The method according to claim 1, wherein the buffer comprises more than one component, and step b) comprises evaluating a decrease of interfacial tension between each component of the buffer and the lubricant.

3. A method to select a lubricant for a container intended to store a protein-based formulation, comprising:
    a) providing at least one lubricant to be investigated;
    b) evaluating the stability of the protein-based formulation relative to said at least one lubricant by the method according to claim 2;
    c) determining sensitivity of the protein-based formulation to the interaction identified in step b); and
    d) selecting a lubricant causing a non-sensitive interaction with the protein-based formulation or adapting the protein-based formulation by a method comprising the steps of:

i) selecting an adjuvant bringing a higher decrease over time of interfacial tension with the lubricant than the decrease over time of interfacial tension between the protein-based formulation and the lubricant; and ii) improving the stability of the protein-based formulation by adding said selected adjuvant to the formulation.

4. A method to select a lubricant for a container intended to store a protein-based formulation, comprising:

a) providing at least one lubricant to be investigated;

b) evaluating the stability of the protein-based formulation relative to said at least one lubricant by the method according to claim 2;

c) determining sensitivity of the protein-based formulation to the interaction identified in step b); and d) selecting a lubricant causing a non-sensitive interaction with the protein-based formulation or adapting the protein-based formulation by a method comprising the steps of:

i) selecting an adjuvant capable of complexing the protein of the protein-based formulation; and ii) improving the stability of the protein-based formulation by adding said adjuvant to the protein-based formulation so as to at least partially reduce the decrease over time of interfacial tension between the protein-based formulation and the lubricant.

5. A method to improve the stability of a protein-based formulation relative to a lubricant of a lubricated container in which said formulation is to be stored, comprising:

a) evaluating the stability of a protein-based formulation relative to said lubricant by the method according to claim 1;

b) selecting an adjuvant bringing a higher decrease over time of interfacial tension with the lubricant than the decrease over time of interfacial tension between protein-based formulation and the lubricant; and c) improving the stability of the protein-based formulation by adding said selected adjuvant to the formulation.

6. The method according to claim 5, wherein the adjuvant is a surfactant.

7. A method to improve the stability of a protein-based formulation relative to a lubricant of a lubricated container in which said formulation is to be stored, comprising:

a) evaluating the stability of a protein-based formulation relative to said lubricant by the method according to claim 1;

b) selecting an adjuvant capable of complexing the protein, peptide, and/or protein-derivative of the protein-based formulation; and c) improving the stability of the protein-based formulation by adding said adjuvant to the protein-based formulation so as to at least partially reduce the decrease over time of interfacial tension between the protein-based formulation and the lubricant.

8. The method according to claim 7, wherein the added adjuvant is a salt.

* * * * *